United States Patent [19]

Lee

[11] 4,183,256

[45] Jan. 15, 1980

[54] VARIABLE RATIO ANGULAR SPEED CONVERTER

[75] Inventor: Arnold St. J. Lee, Red Bank, N.J.

[73] Assignee: Milstein Medical Research Foundation, Inc., New York, N.Y.

[21] Appl. No.: 867,040

[22] Filed: Jan. 5, 1978

Related U.S. Application Data

[62] Division of Ser. No. 750,189, Dec. 13, 1976, Pat. No. 4,085,747.

[51] Int. Cl.² ............................................. F16H 3/32
[52] U.S. Cl. ...................................................... 74/349
[58] Field of Search .................................. 74/348, 349

[56] References Cited

U.S. PATENT DOCUMENTS

| | | | |
|---|---|---|---|
| 1,967,559 | 7/1934 | Schreck | 74/348 |
| 2,662,417 | 12/1953 | Mascherpa | 74/348 X |
| 2,986,951 | 6/1961 | Carriol | 74/348 |
| 3,885,473 | 5/1975 | Stratienko | 74/349 |

FOREIGN PATENT DOCUMENTS

| | | | |
|---|---|---|---|
| 12251 | 6/1909 | Denmark | 74/349 |
| 1550710 | 7/1969 | Fed. Rep. of Germany | 74/348 |

*Primary Examiner*—C. J. Husar
*Assistant Examiner*—Lance W. Chandler

[57] ABSTRACT

A variable-ratio angular speed converter of the gear box type is arranged so that each speed reduction setting on the output shaft is a prescribed fraction of the speed reduction of the next-preceding setting. A first tapered gear cluster is fixedly supported on the input shaft, while a plurality of similar second clusters are supported in spaced relation for rotation on an intermediate shaft. Successive speed reductions of the same nominal ratio are imparted (1) between the first cluster on the input shaft and the first second cluster on the intermediate shaft and (2) between successive second clusters on the intermediate shaft. A housing adjustably supported on the output shaft has a selector gear for engaging an arbitrary one of the gears on any of the first and second clusters.

4 Claims, 2 Drawing Figures

VARIABLE RATIO ANGULAR SPEED CONVERTER

This is a division of copending application Ser. No. 750,189, filed Dec. 13, 1976 now U.S. Pat. No. 4,085,747.

BACKGROUND OF THE INVENTION

The invention relates to variable-ratio angular speed converters, such as speed-changeable gearing.

One known type of arrangement for effecting an adjustable angular speed ratio between input and output shafts is described in U.S. Pat. No. 2,662,417, issued to A. Mascherpa on Dec. 15, 1953. In this scheme, a selector gear disposed on an auxiliary shaft is in constant engagement with a drive gear on the input shaft. The selector gear is pivotable toward and away from a single tapered gear cluster on the output shaft, and is laterally movable along the cluster. By continually rotating a lever-associated knob in a fixed direction, the selector gear is successively (1) pivoted out of engagement with a first gear of the cluster representative of a first speed setting of the arrangement, (2) moved laterally along the cluster to a point opposite a second gear of the cluster representative of a second speed setting of the arrangement, and (3) pivoted into engagement with such second gear to establish such second speed setting.

It is apparent that such arrangement, given a sufficiently large number of gears on the single cluster, can be adjusted to a wide range of speeds on the output shaft. However, it is not adapted to provide an invariant relation between any particular speed setting on the output shaft and the adjacent setting.

SUMMARY OF THE INVENTION

The arrangement of the present invention provides a gear box-type speed conversion arrangement having facilities for selecting one of N discrete, successive speed reduction settings between its input and output shafts. The gear box is so configured that each speed reduction setting is a prescribed fraction of the speed reduction of the next-preceding setting.

In an illustrative embodiment which, like the above-described Mascherpa patent, employs an auxiliary or intermediate shaft, one of a plurality of tapered gear clusters is affixed to the input shaft, and the remainder of such clusters are individually and successively supported for rotation on the intermediate shaft. A first gear carrier couples the first cluster on the input shaft to the initial cluster on the intermediate shaft to impart an angular speed reduction of a prescribed nominal ratio between such clusters, and a plurality of additional gear carriers are individually provided for respectively coupling each successive pair of clusters on the intermediate shaft to impart the same nominal speed reduction therebetween. A housing is supported for pivotal movement around and sliding movement along the output shaft, and carries a gear arrangement for selective engagement with any of the gears of the clusters on the input and intermediate shafts.

Such a configuration is ideally suited, e.g., for driving the plunger of the syringe barrel of an infusion pump, since extremely fine control of the settings of the drug dose rate can be accomplished by coupling the syringe barrel plunger to the output shaft of the gear box.

BRIEF DESCRIPTION OF THE DRAWING

The invention is further set forth in the following detailed description taken in conjunction with the appended drawing, in which.

DETAILED DESCRIPTION

Figure 1:
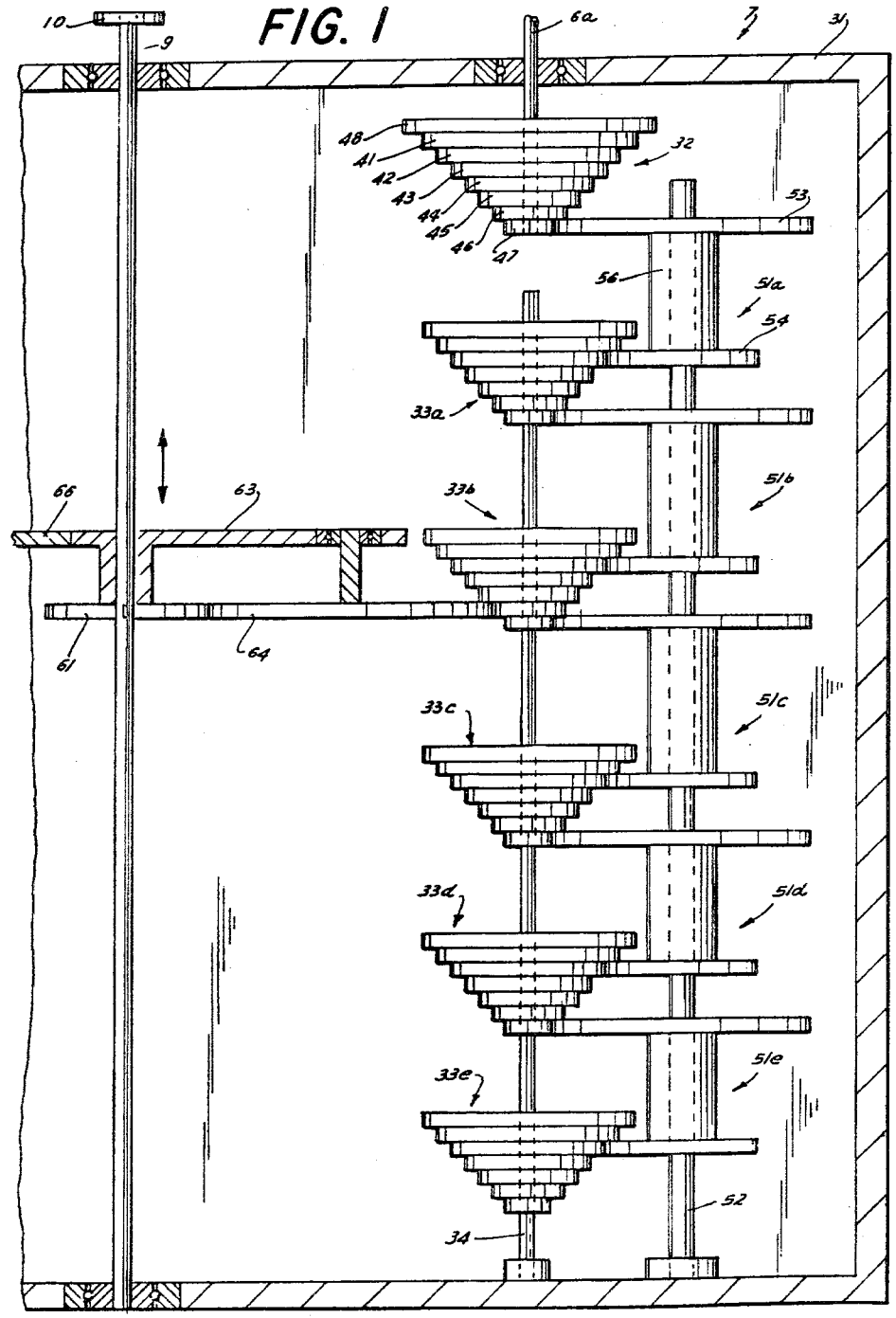
FIG. 1 is an elevation view of a discretely adjustable angular speed converter constructed in accordance with the invention and embodied as a gear box.
Figure 2:
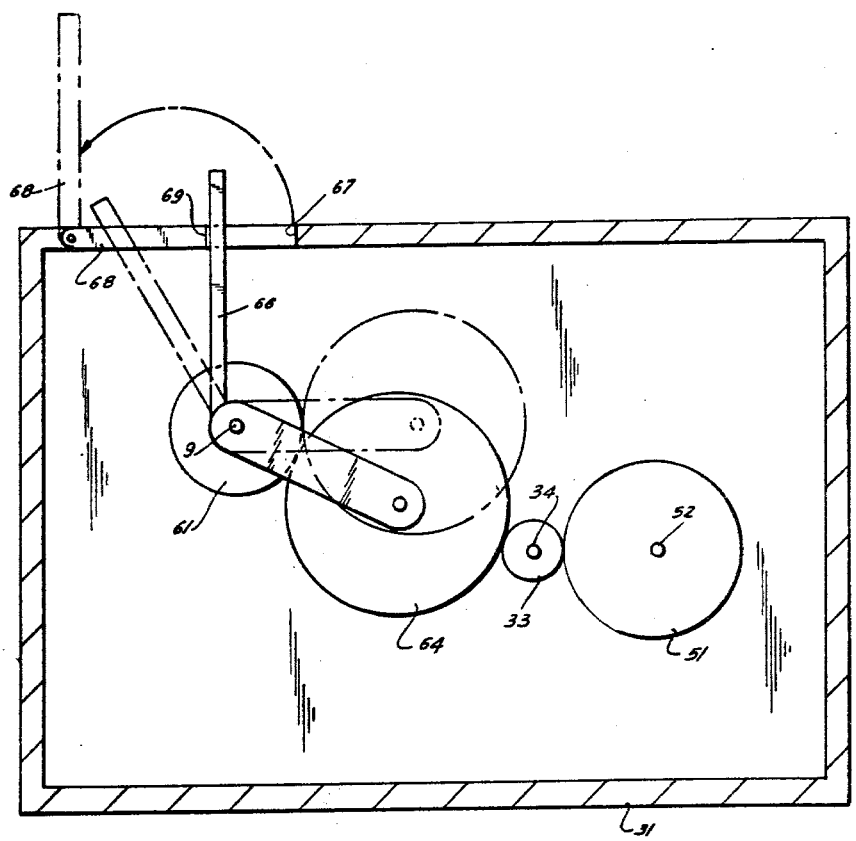
FIG. 2 is a top view of the speed converter of FIG. 1, illustrating additional facilities for the interlocking of the converter.

Referring now to the drawing,

The novel gear box (designated 7) shown in FIGS. 1 and 2, which has an input shaft 6a and an output shaft 9, has wide application as a flexible and efficient speed conversion device because of its capability of reducing its speed at any one of its arbitrary settings by a constant fraction to obtain the next-succeeding setting. As a result, the steps of speed increment provided thereby are related in a constant manner to the speed of the next-preceding step, as well as to the speed of the input shaft.

Illustratively, the gear box constituting the converter 7 in FIGS. 1 and 2 includes an enclosure 31 for housing a plurality of gear clusters subdivided into a first cluster 32 and a plurality (illustratively 5) of second clusters 33a–33e. Each of the clusters 32 and 33 includes, in the arrangement depicted, seven rigidly connected gears 41–47 which are disposed in longitudinally successive relation and which individually bear successively smaller numbers of teeth on their periphery. In addition, the cluster 32 has an eighth gear 48, such gear being larger than any of the remaining gears 41–47 and disposed in contact with the associated first gear 41 of the cluster 32 as shown.

The cluster 32 is rigidly secured to the input shaft 6a of the converter 7, which shaft is rotatably supported in the enclosure 31. The remaining clusters 33a–33e are individually mounted for free rotation about a first auxiliary shaft 34, which is fixedly mounted in the enclosure 31 in alignment with the input shaft. The clusters 33a–33e are longitudinally spaced at equal intervals along the shaft 34.

A plurality of gear carriers 51a–51e, in the form of idler pairs, are individually and successively supported for rotation on a second auxiliary shaft 52, which is fixedly supported in the enclosure 31 in parallel spaced relation to the first auxiliary shaft 34 and the input shaft. Each of the carriers 51 includes an upper gear 53 and a lower gear 54 coupled to respectively opposite ends of a central abutment member 56. The gear 53 is provided with twice the number of teeth as the gear 47. The gear 54 has the same number of teeth as the gear 43. The shaft 52 is so spaced from the adjacent shaft 34 that, taking the carrier 51a as illustrative, the associated upper gear 53 is in engagement with the smallest gear 47 on the cluster 32 while the associated lower gear 54 of the carrier 51a is in engagement with the third gear 43 of the initial second cluster 33a on the shaft 34. Since the cluster 32 rotates at the speed of the input shaft, and since the cluster 33a and the carrier 51a are individually mounted for rotation on their respective shafts, the carrier 51a will be effective to provide a 2:1 speed reduction between the first cluster 32 (and thus the input shaft) and the initial second cluster 33a.

In like manner, the upper gears 53 of each of the remaining carriers 51b–51e are individually in engagement with the smallest gears 47 of the clusters 33a–33d, while the lower gears 54 of the clusters 51b–51e are individually in engagement with the third gears 43 of the clusters 33b–33e.

With such arrangement, the cluster 33b will rotate at one-half the speed of the cluster 33a; the cluster 33c will rotate at one-half the speed of the cluster 33b; and so on.

The output shaft 9 of the converter 7 is splined along its length and is supported for rotation in the enclosure 31. In order to transmit the motion of a selected one of the gears on the rotating clusters 32 and 33 to the output shaft 9, an output gear 61 is splined to the shaft 9 in such a manner that such gear 61 can be moved along the shaft 9 into transverse alignment with any of the total of 48 individual gears on the clusters 32 and 33.

The output gear 61 is supported for rotation in an abutment member 62, which is secured on its opposite end to a carrier member 63. The abutment member 62 and the carrier member 63 individually have apertures therein which are larger than the largest diameter of the splined shaft 9, so that such members may be pivoted about the shaft 9 independently of the output gear 61 rotatably supported therein. The carrier member 63 is further adapted to rotatably support an auxiliary gear 64, which is positioned in engagement with the output gear 61 and which is adapted to directly engage one of the 43 gears on the clusters 32 and 33a when the carrier member 63 is suitably pivoted toward such clusters in the manner shown in FIG. 5. The pivoting of the carrier member 63 is accomplished by means of an attached handle 66, which projects through an opening 67 in the enclosure 31 to cooperate with a spring-loaded door 68 to effect an interlock operation, the door 68 normally being biased into a position extending transversely across and closing the opening 67.

When the handle 66 is in an operative position, shown in solid lines in FIG. 2, the auxiliary gear is maintained in firm engagement with the selected one of the gears on the clusters 32 and 33. Conversely, when the handle is moved counterclockwise from its solid-line position to the inoperative or dotted-line position shown in FIG. 2, the auxiliary gear 64 is placed out of engagement with the clusters.

The spring-loaded door 68 extends in a not-illustrated manner along the enclosure 31 parallel to the output shaft 9, and is provided at longitudinally spaced intervals with a series of 43 staggered transverse steps, one of which is depicted in FIG. 2 and designated at 69.

The step 69 is so positioned that if for any reason the auxiliary gear 64 is not fully engaged with one of the gears on the clusters 32 and 33 (i.e., so that the handle 66 is not completely in its solid-line position shown), the step 69 will contact the handle and prevent the door from closing.

Once the door 68 is in its closed position, the step 69 serves to confine the handle 66 in its operative, solid-line position. In order for the handle to be moved counterclockwise into its inoperative position, it is necessary to first open the door 68 against the biasing force thereon.

The relative number of teeth on the common gears 41–47 of all of the clusters 32 and 33, and the number of teeth of the extra gear 48 on the cluster 32, are so selected, in cooperation with the 2:1 speed reduction between the clusters 32 and 33a, the clusters 33a and 33b, and so forth, that the speed of rotation of the splined output shaft 9 will be varied by successively smaller increments as the auxiliary gear 64 engages successively lower ones of the gears on the clusters shown in FIG. 1. Quantitatively, the speed of the shaft 9 when the gear 64 engages the gear 41 on the cluster 32 is selected to be about 90% of the speed of such output shaft when the gear 64 engages the upper gear 48 on the cluster 32. In like manner, the speed of the output shaft 9 when the gear 64 engages the gear 42 of the cluster 32 is selected to be about 90% of the speed of such output shaft when the gear 64 engages the next-higher gear 41; and so forth. The numerical increment in speed between successive settings, therefore, will be come finer and finer as the gear 64 proceeds downwardly along the clusters.

Table 1 below illustrates a typical set of relationships between the numbers of teeth of each of the gears on the several clusters shown in FIG. 1 and the corresponding relative rotational speed of the output shaft 9 corresponding to the engagement by the auxiliary gear 64 of each such cluster gear, with the engagement of the uppermost gear 48 corresponding to an arbitrary reference value of 128.

TABLE I

| Cluster | Gear | Number of Teeth | Relative Speed of Output Shaft | |
|---|---|---|---|---|
| 32 | 48 | 96 | 128 | (extra speed) |
| | 41 | 87 | 116 | |
| | 42 | 79 | 105 | |
| | 43 | 72 | 96 | |
| | 44 | 65 | 87 | |
| | 45 | 59 | 79 | |
| | 46 | 53 | 71 | |
| | 47 | 48 | 64 | |
| 33a | 41 | 87 | 58 | |
| | 42 | 79 | 53 | |
| | 43 | 72 | 48 | |
| | 44 | 65 | 43 | |
| | 45 | 59 | 39 | |
| | 46 | 53 | 35 | |
| | 47 | 48 | 32 | |
| 33b | 41 | 87 | 29 | |
| | 42 | 79 | 26 | |
| | 43 | 72 | 24 | |
| | 44 | 65 | 22 | |
| | 45 | 59 | 20 | |
| | 46 | 53 | 18 | |
| | 47 | 48 | 16 | |
| 33c | 41 | 87 | 14.5 | |
| | 42 | 79 | 13 | |
| | 43 | 72 | 12 | |
| | 44 | 65 | 11 | |
| | 45 | 59 | 10 | |
| | 46 | 53 | 9 | |
| | 47 | 48 | 8 | |
| 33d | 41 | 87 | 7.3 | |
| | 42 | 79 | 6.6 | |
| | 43 | 72 | 6.0 | |
| | 44 | 65 | 5.4 | |
| | 45 | 59 | 4.9 | |
| | 46 | 53 | 4.4 | |
| | 47 | 48 | 4.0 | |
| 33e | 41 | 87 | 3.6 | |
| | 42 | 79 | 3.3 | |
| | 43 | 72 | 3.0 | |
| | 44 | 65 | 2.7 | |
| | 45 | 59 | 2.46 | |
| | 46 | 53 | 2.2 | |
| | 47 | 48 | 2.0 | |

As clearly evident from Table 1, an overall speed change of 64:1 is obtainable with the 43 settings of the gear box shown in FIG. 1, with the increments between the speeds established by the last cluster 33e being significantly smaller than the increments established by the gears on the cluster 32.

In the foregoing, an illustrative arrangement of the invention has been described. Many variations and modifications will now occur to those skilled in the art. It is accordingly desired that the scope of the appended claims not be limited to the specific disclosure herein contained.

What is claimed is:

1. In an apparatus for effecting an angular speed conversion between a first input shaft and a second output shaft, the conversion effecting apparatus comprising, in combination, a plurality of gear clusters each having a plurality of gears fixedly disposed in successive, axially spaced concentric relation, the successive gears in each cluster having progressively smaller numbers of teeth, means for fixedly mounting a first one of the clusters to the first shaft, a third shaft, means for independently and successively mounting each of the remaining clusters for rotation on the third shaft in an axially spaced relation, means coupling the first cluster to an initial one of the remaining clusters in the succession on the third shaft for imparting an angular speed reduction of a prescribed nominal ratio between the first cluster and the initial cluster on the second shaft, a plurality of means each coupled between one of the clusters on the third shaft and the next-succeeding one of the clusters on the third shaft for imparting an angular speed reduction of said nominal ratio between the associated clusters, and speed ratio selection means carried on the second shaft for engaging an arbitrary one of the gears of any of the gear clusters on the first and third shafts.

2. Apparatus as defined in claim 1, in which the first and third shafts are disposed in axially aligned relation, in which the second shaft is supported in parallel spaced relation to the aligned first and third shafts opposite the clusters thereon, and in which the speed ratio selection means comprises, in combination, a housing mounted for sliding movement on and pivotal movement about the second shaft toward and away from the aligned first and third shafts, and gear means carried in the housing for engagement with the arbitrary one of the cluster gears.

3. Apparatus as defined in claim 2, in which the apparatus further comprises, in combination, an enclosure surrounding the clusters on the third shaft and the housing on the second shaft, the enclosure having therein an access opening bounded between first and second opposed walls, handle means connected to the housing for pivoting the housing about the second shaft between a first position in which the associated gear means are in engagement with one of the cluster gears and a second position in which the gear means are out of engagement with the cluster gears, the handle means extending outwardly through the access opening and toward the first wall of the access opening when in the first position, a spring-loaded door pivotally mounted to the enclosure and biased for movement across the access opening into a closed position, and means disposed on the handle means and operable when the door moves toward its closed position for engaging the handle means to prevent the door from closing unless the handle means is in its first position.

4. In an apparatus for effecting an angular speed conversion between a first input shaft and a second output shaft, the conversion-effecting apparatus comprising, in combination, a first gear cluster and a plurality of second gear clusters each having a plurality of gears fixedly disposed in successive, axially spaced concentric relation, the successive gears in each cluster having progressively smaller numbers of teeth, means for fixedly mounting the first cluster on the first shaft, means successively supporting the second clusters in mutually spaced axial alignment with the first cluster for independent relative rotation with respect to the first shaft, means coupling the first cluster to an initial one of the second clusters in the succession for imparting an angular speed reduction of a prescribed nominal ratio between the first cluster and the initial second cluster, a plurality of means individually coupled between each of the second clusters and the adjacent one of the second clusters for imparting an angular speed reduction of said nominal ratio between the associated second clusters, and speed ratio selection means carried on the second shaft for engaging an arbitrary one of the gears of any of the first and second clusters.

* * * * *